United States Patent
Lee et al.

(10) Patent No.: US 11,400,181 B2
(45) Date of Patent: Aug. 2, 2022

(54) POLYMER INTERLOCK SUPPORT STRUCTURE AND METHOD OF MANUFACTURE THEREOF

(71) Applicant: Howmedica Osteonics Corp., Mahwah, NJ (US)

(72) Inventors: Reginald Lee, West Chester, PA (US); Philip Harris Frank, Maplewood, NJ (US); Alvin Perez, Ringwood, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 16/003,411

(22) Filed: Jun. 8, 2018

(65) Prior Publication Data

US 2018/0353642 A1 Dec. 13, 2018

Related U.S. Application Data

(60) Provisional application No. 62/517,456, filed on Jun. 9, 2017.

(51) Int. Cl.
*A61L 27/16* (2006.01)
*A61L 27/04* (2006.01)
(Continued)

(52) U.S. Cl.
CPC ............... *A61L 27/16* (2013.01); *A61F 2/28* (2013.01); *A61F 2/30907* (2013.01); *A61F 2/34* (2013.01); *A61F 2/389* (2013.01); *A61F 2/3877* (2013.01); *A61F 2/4081* (2013.01); *A61F 2/4202* (2013.01); *A61F 2/4225* (2013.01); *A61F 2/4261* (2013.01); *A61F 2/44* (2013.01); *A61L 27/04* (2013.01); *A61L 27/56* (2013.01);
(Continued)

(58) Field of Classification Search
CPC .... A61F 2/28–447; A61F 2/34; A61F 2/3877; A61F 2/389; A61F 2/4081; A61F 2/4202; A61F 2/4225; A61F 2/4261; A61F 2/44
See application file for complete search history.

(56) References Cited

U.S. PATENT DOCUMENTS 3,906,550 A 9/1975 Rostoker et al.
4,550,448 A 11/1985 Kenna
(Continued)

OTHER PUBLICATIONS

European Search Report for EP Application No. 18176659.3, dated Oct. 17, 2018.

*Primary Examiner* — Nicholas J Plionis
(74) *Attorney, Agent, or Firm* — Lerner, David, Littenberg, Krumholz & Mentlik, LLP

(57) ABSTRACT

An orthopedic implant includes a porous insert having a first insert portion having a first insert thickness and a second insert portion having a second insert thickness. The implant includes a non-metallic structure having a first non-metallic portion having a first non-metallic thickness and a second non-metallic portion having a second non-metallic thickness. The first non-metallic portion is attached to the first insert portion and the second non-metallic portion is attached to the second insert portion. Either or both of the second insert thickness being different from the first insert thickness and the second non-metallic thickness being different from the first non-metallic thickness. The porous insert includes a porous projection extending into the non-metallic structure.

22 Claims, 3 Drawing Sheets

(51) Int. Cl.
- *A61F 2/28* (2006.01)
- *A61F 2/34* (2006.01)
- *A61F 2/38* (2006.01)
- *A61F 2/40* (2006.01)
- *A61F 2/42* (2006.01)
- *A61F 2/44* (2006.01)
- *A61L 27/56* (2006.01)
- *A61F 2/30* (2006.01)

(52) U.S. Cl.
CPC ... *A61F 2/3094* (2013.01); *A61F 2002/30011* (2013.01); *A61F 2002/3028* (2013.01); *A61F 2002/3092* (2013.01); *A61F 2002/3093* (2013.01); *A61F 2002/30331* (2013.01); *A61F 2002/30609* (2013.01); *A61F 2002/30733* (2013.01); *A61F 2002/30784* (2013.01); *A61F 2002/30971* (2013.01); *A61F 2002/30985* (2013.01); *A61L 2430/02* (2013.01); *A61L 2430/38* (2013.01)

(56) References Cited

U.S. PATENT DOCUMENTS

| | | |
|---|---|---|
| 4,878,916 A | 11/1989 | Rhenter et al. |
| 4,904,261 A | 2/1990 | Dove et al. |
| 4,919,667 A | 4/1990 | Richmond |
| 4,944,756 A | 7/1990 | Kenna |
| 4,997,445 A | 3/1991 | Hodorek |
| 5,330,533 A | 7/1994 | Walker et al. |
| 5,879,398 A | 3/1999 | Swarts et al. |
| 6,087,553 A * | 7/2000 | Cohen .................. C08L 23/06 623/22.21 |
| 6,277,150 B1 | 8/2001 | Crawley et al. |
| 6,325,829 B1 | 12/2001 | Schmotzer |
| 6,923,831 B2 | 8/2005 | Fell et al. |
| 6,994,730 B2 | 2/2006 | Posner |
| 7,326,253 B2 | 2/2008 | Synder et al. |
| 7,341,602 B2 | 3/2008 | Fell et al. |
| 7,537,664 B2 | 5/2009 | O'Neill et al. |
| 7,597,715 B2 | 10/2009 | Brown et al. |
| 8,080,059 B2 | 12/2011 | Fell |
| 8,556,981 B2 | 10/2013 | Jones et al. |
| 8,652,212 B2 | 2/2014 | Case et al. |
| 8,728,387 B2 | 5/2014 | Jones et al. |
| 8,864,826 B2 | 10/2014 | Pressacco |
| 8,911,501 B2 | 12/2014 | Irwin et al. |
| 9,017,416 B2 | 4/2015 | McMinn |
| 9,089,431 B2 | 7/2015 | Grohowski, Jr. |
| 9,135,374 B2 | 9/2015 | Jones et al. |
| 9,180,010 B2 | 11/2015 | Dong et al. |
| 9,237,950 B2 | 1/2016 | Hensley et al. |
| 9,283,079 B2 | 3/2016 | McMinn |
| 9,345,578 B2 | 5/2016 | Collazo et al. |
| 9,364,896 B2 | 6/2016 | Christensen et al. |
| 9,445,909 B2 | 9/2016 | Cohen et al. |
| 9,456,901 B2 | 10/2016 | Jones et al. |
| 9,649,193 B2 | 5/2017 | McMinn |
| 9,744,044 B2 | 8/2017 | Cohen et al. |
| 9,801,974 B2 | 10/2017 | Landon |
| 9,956,081 B2 | 5/2018 | McMinn |
| 2004/0133275 A1 * | 7/2004 | Mansmann ......... A61F 2/30756 623/14.12 |
| 2004/0262809 A1 * | 12/2004 | Smith ................. A61L 27/56 264/259 |
| 2005/0112397 A1 | 5/2005 | Rolfe et al. |
| 2006/0147332 A1 | 7/2006 | Jones et al. |
| 2007/0142914 A1 * | 6/2007 | Jones ................. A61F 2/30907 623/14.13 |
| 2008/0167723 A1 * | 7/2008 | Acker ................. A61F 2/30767 623/22.4 |
| 2010/0042226 A1 | 2/2010 | Nebosky et al. |
| 2010/0100189 A1 * | 4/2010 | Metzger ................. A61F 2/38 623/20.14 |
| 2010/0331981 A1 * | 12/2010 | Mohammed ........ A61F 2/30721 623/16.11 |
| 2011/0035018 A1 * | 2/2011 | Deffenbaugh .......... A61F 2/389 623/20.28 |
| 2011/0089599 A1 | 4/2011 | Denoziere et al. |
| 2011/0257753 A1 | 10/2011 | Gordon et al. |
| 2013/0264749 A1 * | 10/2013 | Jones ................. G06F 30/00 264/497 |
| 2014/0257507 A1 * | 9/2014 | Wang ................. A61F 2/3877 623/20.34 |
| 2014/0309746 A1 | 10/2014 | Fang et al. |
| 2016/0220376 A1 | 8/2016 | Li et al. |
| 2016/0220377 A1 | 8/2016 | Li et al. |

* cited by examiner

POLYMER INTERLOCK SUPPORT STRUCTURE AND METHOD OF MANUFACTURE THEREOF

CROSS REFERENCE TO RELATED APPLICATIONS

The present application is a non-provisional which claims the benefit of U.S. Provisional Application No. 62/517,456, filed Jun. 9, 2017, the disclosure of which is incorporated herein by reference.

BACKGROUND OF THE INVENTION

The present invention generally relates to a support structure for a bearing surface, and in particular to a device having an at least partially porous structure to support a bearing surface.

Generally, orthopedic devices are mated with natural bone using bone cement or by providing a rough or porous surface on the device for bone tissue ingrowth, in which such orthopedic devices are commonly referred to as cementless implants. Cementless implants often utilize a plurality of layers, each configured for their own purpose. For example, the tibial component of the Triathlon® Total Knee System by Stryker Corporation optionally includes the Triathlon® Tritanium® Tibial Baseplate having a metallic insert with a porous layer for bone ingrowth, a substantially solid intermediate layer, and a porous bearing support layer into which a polymeric layer is molded to form a bearing surface for articulation of a femoral component. The intermediate layer prevents interdigitation of the polymeric layer from the bearing support layer to the porous bone ingrowth layer.

In cementless implants having a plurality of layers, the thickness of these implants is generally greater than the thickness of their cemented counterparts. This increased thickness requires more bone removal and is more invasive to the natural tissue than that necessary for cemented implants.

Thus, there is a need for a cementless implant having a thinner profile without sacrificing strength or implant stability.

BRIEF SUMMARY OF THE INVENTION

In accordance with an aspect, a porous structure, which preferably may be a medical implant, may include a metallic insert having a solid or substantially solid layer and an interlock layer attached to the solid or substantially solid layer. The metallic insert may include a tapered surface such that a portion of the insert has a thinner thickness and a portion has a thicker thickness. In some such arrangements, a central section of the solid or substantially solid layer may be thinner than other sections of the structure. The interlock layer may be interlocked along a length of the interlock layer with a polymeric bearing structure defining a bearing surface. The interlock layer may include one or more projections extending from the thicker thickness portion of the metallic insert and into a portion of the bearing structure. In this manner, the thicker thickness portion of the interlock layer may be reinforced to compensate for a thinner thickness portion of the interlock layer that may be interlocked with the bearing structure. As such, the thickness of the bearing structure may be thicker where the metallic insert is thinner such that the thickness of the porous structure may be uniform. Further, the interlock layer, and in particular the projection or projections of the interlock layer, may provide support for the bearing structure where the bearing structure is thinner.

In some arrangements, the metallic insert may further include a porous first layer, which preferably may be a bone ingrowth layer and which may be attached to a side of the solid or substantially solid layer opposite the interlock layer. In some arrangements, the interlock layer may have a porosity sufficient to allow for interdigitation of a flowable polymeric material into the interlock layer and subsequent hardening of the polymer material, which may be by compression molding, injection molding, or a heat forming process, to form the bearing structure. In some such arrangements, the solid or substantially solid layer may prevent flow of the polymeric material from the interlock layer to the porous first layer. In arrangements with or without the porous first layer, the metallic insert may be monolithic in which the layers of the insert are integrated such that the layers are inseparable. In some arrangements, the metallic insert may be formed using an additive manufacturing process, which preferably may be a powder-fed process. In such arrangements, all of the layers of the metallic insert may be formed during a continuous process.

In accordance with another aspect, the bearing structure may extend the entire thickness of the porous structure.

In accordance with another aspect, an orthopedic implant may include a porous insert having a first insert portion having a first insert thickness and a second insert portion having a second insert thickness. The implant may include a non-metallic structure having a first non-metallic portion with a first non-metallic thickness and a second non-metallic portion with a second non-metallic thickness. The first non-metallic portion may be attached to the first insert portion, and the second non-metallic portion may be attached to the second insert portion. The second insert thickness may be different from the first insert thickness. and the second non-metallic thickness may be different from the first non-metallic thickness. The porous insert may include a porous projection that may extend into the non-metallic structure. The first insert thickness, the second insert thickness, the first non-metallic thickness, and the second non-metallic thickness may all be defined in the same direction.

In some arrangements, the porous projection may have a perimeter surrounded by the non-metallic structure. In some such arrangements, the porous insert may include a porous first layer, an intermediate layer attached to the first layer, and a porous second layer attached to the intermediate layer on a side of the intermediate layer opposite the first layer. The porous projection may extend from the second layer. In some such arrangements, the implant may include a superior surface and an inferior surface opposite the superior surface. The first, intermediate, and second layers and the non-metallic structure may each have a maximum thickness defined in superior-inferior directions along an axis passing through the superior and inferior surfaces. The maximum thickness of the non-metallic structure may be greater than the thickness of each of the other layers.

In some arrangements, the first layer may be a bone ingrowth layer that may have a porosity sufficient to promote bone ingrowth.

In some arrangements, the non-metallic structure may be made of a polyethylene.

In some arrangements, the implant may have a superior surface and an inferior surface opposite the superior surface. A section of the non-metallic structure may extend from the superior surface to the inferior surface of the implant.

In some arrangements, the first non-metallic thickness may be less than the second non-metallic thickness. The projection may extend into the first non-metallic portion of the non-metallic structure.

In some arrangements, the insert may include a metallic tapered surface. The non-metallic structure may include a non-metallic tapered surface, which may extend along the metallic tapered surface between the first non-metallic portion and the second non-metallic portion.

In some arrangements, the first insert portion and the second insert portion may define an insert width. The non-metallic structure may extend along the entirety of the insert width.

In some arrangements, the non-metallic structure may be a bearing having a bearing surface.

In some arrangements, the implant may be a tibial component, a glenoid component, a patellar component, a wrist implant, a foot implant, an ankle implant, a spinal implant, or an acetabular cup.

In some arrangements, the first insert thickness and the second insert thickness may be the same.

In some arrangements, the first non-metallic thickness and the second non-metallic thickness may be the same.

In accordance with another aspect, an implant may have a superior surface and an inferior surface opposite the inferior surface. The implant may include a polymeric structure and a metallic support structure. The support structure may include a base and may include a porous projection. The projection may extend from the base and into the polymeric structure. At least a portion of the polymeric structure may extend through the support structure from the superior surface to the inferior surface.

In some arrangements, the implant may include an intermediate layer and a bone ingrowth layer. The intermediate layer may be located between and may be inseparable from the bone ingrowth layer and the support structure. In some such arrangements, the intermediate layer may inhibit the polymeric structure from translating through the support structure and into the bone ingrowth layer.

In some such arrangements, the bone ingrowth layer may have a porosity sufficient to promote bone ingrowth.

In some such arrangements, a porosity of the bone ingrowth layer may be different than a porosity of the support structure.

In some such arrangements, the support structure, the intermediate layer, and the bone ingrowth layer may be made from a metal selected from the group consisting of titanium, titanium alloy, cobalt chrome alloys, stainless steel, and tantalum and niobium.

In some arrangements, the implant may be a tibial component. In some arrangements, the implant may be a glenoid component.

In some arrangements, the projection of the support structure may have a perimeter surrounded by the polymeric structure.

In some arrangements, the polymeric structure may interdigitate and interlock with the support structure.

In some arrangements, the polymeric structure may define a bearing surface for placement against bone.

In accordance with another aspect, a porous structure may include a first component portion having a first component thickness and a second component portion having a second component thickness. The porous structure may include a non-metallic structure having a first non-metallic portion with a first non-metallic thickness and a second non-metallic portion with a second non-metallic thickness. The first non-metallic portion may be attached to the first component portion, and the second non-metallic portion may be attached to the second component portion. The second component thickness may be different from the first component thickness, and the second non-metallic thickness may be different from the first non-metallic thickness. The porous component may include a porous projection that may extend into the non-metallic structure. The first component thickness, the second component thickness, the first non-metallic thickness, and the second non-metallic thickness may all be defined in the same direction.

In accordance with another aspect, an orthopedic implant may be produced. In producing the implant, a first layer of metal powder may be deposited. The first layer of metal powder may be scanned with a high energy beam at predetermined locations. Successive layers of the metal powder may be deposited onto respective previous layers of powder. Each successive layer may be scanned until a predetermined metal structure having a first surface and a second surface opposite the first surface is constructed. The predetermined metal structure may have a first metal portion defining a first segment of the second surface and having a first metal thickness. The predetermined metal structure may have a second metal portion defining a second segment of the second surface and having a second metal thickness. The predetermined metal structure may include a porous projection extending from the second segment of the second surface. A polymer may be placed into contact with the first segment of the second surface, the second segment of the second surface, and the porous projection of the predetermined metal structure. The polymer may be cooled such that a first polymeric portion of the polymer adheres to the first segment of the second surface and a second polymeric portion of the polymer adheres to the second segment of the second surface and to the porous projection of the predetermined metal structure. The first polymeric portion may have a first thickness, and the second polymeric portion may have a second polymeric thickness. The second metal thickness may be different from the first metal thickness, and the second polymeric thickness may be different from the first polymeric thickness. The first metal thickness, second metal thickness, first polymeric thickness, and second polymeric thickness may all be defined in a same direction.

In some arrangements, the high energy beam may be a laser beam or an electron beam.

In some arrangements, the high energy beam may be scanned onto the metal powder to form a portion of a plurality of predetermined porous geometries.

In some arrangements, the predetermined metal structure may be placed into a cavity of die. In some such arrangements, the polymer may be deposited onto the second surface of the predetermined metal structure within the cavity of the die. In some such arrangements, pressure and heat may be applied to the polymer in the cavity of the die.

In some arrangements, the predetermined metal structure may include a first layer, an intermediate layer attached to the first layer, and a second layer attached to the intermediate layer on a side of the intermediate layer opposite the first layer. The first and second layers may be porous. The intermediate layer may be solid or substantially solid such that polymer cannot translate through the intermediate layer and into the first layer from the second layer. In some such arrangements, the first layer may have a porosity to allow bone ingrowth.

In some arrangements, the predetermined metal structure may be configured to represent a tibial component, a glenoid component, a patellar component, a foot implant, a hand implant, a spinal implant, or an acetabular cup.

In some arrangements, the polymer may be cooled into the form of a bearing having a bearing surface.

In some arrangements, the polymer may be a polyethylene.

In some arrangements, the first layer and successive layers of metal powder may be sintered or melted.

BRIEF DESCRIPTION OF THE DRAWINGS

A more complete appreciation of the subject matter of the present invention and the various advantages thereof can be realized by reference to the following detailed description and accompanying drawings to which reference is made, in which.

DETAILED DESCRIPTION

Figure 1:
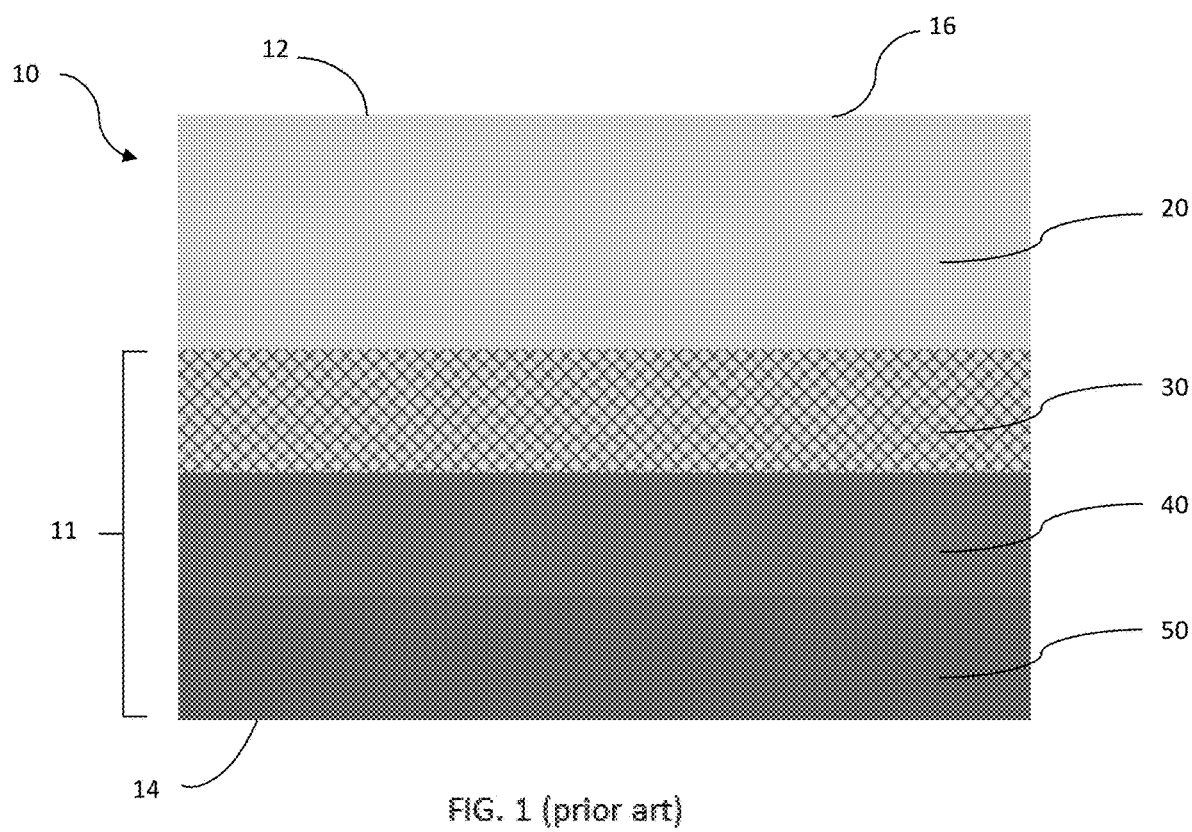
FIG. 1 is a cross-sectional elevation view of a porous structure as known in the prior art.

Referring to FIG. 1, porous structure 10, which is a component of a medical implant in accordance with the prior art, includes monolithic metal insert 11 and bearing structure 20 defining bearing surface 12 extending along superior surface 16. The medical implant may be a tibial component, patellar component of a knee implant, glenoid component of a shoulder implant, an interbody fusion spinal implant, an intervertebral spinal implant, a wrist implant, a foot implant, an ankle implant, or an acetabular cup of a hip implant, as disclosed in U.S. Pat. No 8,728,387, the disclosure of which is hereby incorporated by reference herein.

Insert 11 includes porous first layer 50 defining outer, inferior surface 14, porous interlock layer 30, and intermediate layer 40 between and integral with the first layer and the interlock layer such that the intermediate layer is inseparable from the first layer and the interlock layer. Interlock layer 30 may have a porosity that allows for a flowable polymeric material to interdigitate into and adhere to the construct of the interlock layer. Bearing structure 20 may be made of any appropriate material, including ultra-high molecular weight polyethylene ("UHMWPE"), polyether ether ketone ("PEEK"), polyurethane, or other flowable polymer, that may be interdigitated into interlock layer 30, such as by a compression molding process or an injection molding process. In this manner, the interlock layer acts as a bearing support structure that supports the polymeric material. As in the example shown, intermediate layer 40 may be solid or substantially solid such that bearing structure 20 does not flow from interlock layer 30 to first layer 50. In one example, porous structure 10 is a medical implant in which first layer 50 is a bone ingrowth layer defining outer surface 14 that may be placed against bone stock. Generally, bearing surface 12 of bearing structure 20 is configured to contact a corresponding bearing surface of another component of the medical implant with reduced friction, relative to non-bearing surfaces, during relative movement, which may be either of or both translational and rotational movement, between the surfaces.

As represented in FIG. 1, first layer 50, intermediate layer 40, and interlock layer 30 are each of substantially uniform thicknesses, as measured along a longitudinal axis through each of these layers. As in the example shown, the thickness of bearing structure 20 is often greater than the individual thicknesses of the other three layers to provide adequate strength for the bearing structure.

In preferred arrangements, metallic insert 11 of porous structure 10 may be formed, at least in part, in a layer-by-layer fashion using an additive layer manufacturing (ALM), i.e. 3D printing, process using a high energy beam, such as a laser beam or an electron beam. Such ALM processes preferably may be powder-bed based processes including selective laser sintering (SLS), selective laser melting (SLM), and electron beam melting (EBM), as disclosed in U.S. Pat. No. 7,537,664 ("the '664 Patent") and U.S. Pat. No. 9,456,901 ("the '901 Patent"), the disclosures of each of which are hereby incorporated by reference herein, or other ALM processes such as powder-fed based processes including fused filament fabrication (FFF), e.g., fused deposition modeling (FDM). When utilizing the SLM or EBM processes, insert 11 may be formed using the beam overlap process disclosed in the '664 Patent or may be formed through the use of unit cells as employed in the '901 Patent. In forming insert 11, various metals and metal alloys may be employed including stainless steel, cobalt chromium alloys, titanium and its alloys, tantalum and niobium.

Porous structure 10 may be fabricated at least in part by forming structures having solid or substantially solid as well as porous metallic layers using an additive manufacturing process. In this manner, metallic insert 11 may be made by building porous first layer 50, intermediate layer 40, and interlock layer 30 in a continuous operation. The polymeric material is then attached to the metallic insert.

As in the example of metallic insert 11, porous first layer 50 and interlock layer 30 may be constructed of porous geometries which have been digitally modeled using unit cells, as further described in U.S. Pat. No. 9,180,010 ("the '010 Patent") and U.S. Pat. No. 9,135,374, the disclosures of each of which are hereby incorporated by reference herein. A first layer or portion of a layer of powder is deposited and then scanned with a high energy beam to create a portion of a plurality of predetermined porous geometries, as further described below. Successive layers of powder are then deposited onto previous layers of the powder and then scanned with the high energy beam. The scanning and depositing of successive layers of the powder continues the building process of the predetermined porous geometries. As disclosed herein, by continuing the building process refers not only to a continuation of a porous geometry from a previous layer but also a beginning of a new porous geometry as well as the completion of a porous geometry. The porous geometries of the formed porous layers may define pores that may be interconnecting to provide an interconnected porosity.

The high energy beam may be an electron beam (e-beam) or laser beam and may be applied continuously to the powder or pulsed at a predetermined frequency. In some arrangements, the use of the laser or e-beam melting process may preclude the requirement for subsequent heat treatment of the structure fabricated by the additive manufacturing process. The high energy beam is emitted from a beam-generating apparatus to heat the metal powder sufficiently to sinter and preferably to at least partially melt or melt the metal powder. High energy beam generation equipment for manufacturing such structures may be one of many currently available including the MCP REALIZER, the EOS M270, TRUMPF TRUMAFORM 250, the ARCAM EBM S12, and the like. The beam generation equipment may also be a custom-produced laboratory device.

The pore density, pore size and pore size distribution of the at least partially porous first and interlock layers can be controlled (varied) from one location on the structure to another. Successive powder layers may differ in porosity by varying factors used for scanning powder layers. The porosity of successive layers of powder can be varied by either creating a specific type of unit cell or manipulating various dimensions of a given unit cell. Further, the porosity of each structure is preferably dependent on the function of that structure.

In producing porous first layer 50 and interlock layer 30, the nature of the material formed as a result of laser melting of powdered particles is principally dependent on the thermal profile involved (heating rate, soaking time, cooling rate); the condition of the raw material (size and size distribution of powder particles); and atmospheric conditions (reducing, inert or oxidizing chamber gas).

Porous first layer 50 and interlock layer 30 each may be modeled using a plurality of unit cells that are then filled by struts that may be attached at vertices of the unit cells to define modeled porous geometries. Many configurations of unit cells are possible to give the shape, type, degree and size of porosity required. Unit cell configurations may be dodecahedral, octahedral, diamond, as well as other various regular geometric shapes. Besides such regular geometric shapes, unit cells may be configured to have irregular shapes where various sides and dimensions have little if any repeating sequences. The modeled porous geometries within the unit cells may be configured to constructs that closely mimic the structure of trabecular bone for instance. Unit cells may be space filling, where all the space filled within a three-dimensional model of an object is filled with unit cells, or interconnected, where there may be some space left between cells but the cells are connected together by their edges.

The unit cells may be distributed within the construct in a number of ways. They may be made into a block within a computer automated design (CAD) system, i.e., the frame defining a boundary or boundaries within a CAD model, where the dimensions correspond to the extent of the solid geometry to be fabricated. This block may then be intersected with a wireframe geometry representing a component or other construct to be fabricated to produce a porous cellular representation of the geometry. The unit cells may be deformed so as to drape over an object as disclosed in the '901 Patent, and allow the unit cells to follow the surface of the geometry or so as to conform to the frame of the CAD model as disclosed in the '010 Patent. The cells may be populated through the geometry following the contours of the selected surface.

Modifications to the dimensions of the struts can be used to control the mechanical strength of the porous geometries. Modifications can be in a number of key areas. The strut dimensions can be adjusted by careful selection of build parameters or specifically by changing any of the shape of the cross-section and the length of each strut. The density of the lattice can similarly be adjusted by modifying the density of the unit cells as can the extent and shape of porosity or a combination thereof. The overall design of the unit cells and their corresponding porous geometries will have an effect on the structural performance of a formed construct. For example, the use of dodecahedral unit cells will lead to different mechanical performance as compared with the use of tetrahedral unit cells.

Depending on the material used to create bearing structure 20, the polymeric material may be integrated with interlock layer 30 by compression molding, injection molding, or a heat forming process. If the polymeric material to be used to form bearing structure 20 is UHMWPE or the like, the metallic insert, i.e., the first layer 50, intermediate layer 40, and interlock layer 30, but specifically the interlock layer 30, may be joined to bearing structure 20 by a compression molding process using a matched metal die. The metal insert is placed into a cavity part of a metal die. The polymer powder may then be added to the cavity of the metal die and desirably is dispersed against the interlock layer 30. The cavity of the metal die is sealed and the metal die is then heated to a required temperature. As the temperature of the polymer powder is increased, the polymer powder begins to soften or melt so as to be flowable. Increased pressure onto the polymer powder may also aid in the melting process. Fusion of the polymer powder and attachment to interlock layer 30 is achieved when the acquired application of heat and pressure is reached. Subsequent cooling under pressure allows solidification of the polymer powder, which thus forms bearing structure 20 that is securely attached to interlock layer 30. A final machining operation may be required to complete the construct of bearing structure 20.

In an alternate embodiment, an injection molding process may be carried out in order to fuse the bearing structure 20 to the interlock layer 30. An injection molding process may be preferred when the material used to create the bearing structure 20 is a polyurethane or chopped-fiber-reinforced poly (ETHERETHERKETONE) ("CFR-PEEK"). Similar to the compression molding process, in the injection molding process, the metal insert is secured into a cavity of an injection molding machine and the mold closed. The selected material, e.g., polyurethane or CFR-PEEK, is heated in a barrel of the injection molding machine. Once the selected material is heated in the barrel of the injection mold, the pressure may be applied to the selected material to urge the heated selected material from the barrel into the mold cavity and onto a surface of interlock layer 30. Upon cooling, the selected material is fused to interlock layer 30 so as to form bearing structure 20. Upon cooling, the completed part may be removed from the injection mold and machined if so required. The mold cavity may be configured such that particular features, designs and contours of bearing structure 20 may be formed.

In yet another embodiment, the bearing structure 20 may be formed using a heat forming process. In a heat forming process, materials such as UHMWPE, are supplied as fabricated rod stock suitable for machining Profiles can be produced by machining the fabricated rod stock to represent a near net shape of intended bearing structure 20. Once bearing structure 20 has been produced, both metal insert 11 and the shaped polymer machine part are placed into a mold and heated to the required temperature. Upon application of heat and pressure, the softened polymer is forced into and against the metal insert, specifically interlock layer 30. Upon cooling, solidification takes place and the polymer is secured to the metal insert and specifically interlock layer 30. Further machining may be required if necessary once the part has been allowed to cool and is removed from the mold.

Figure 2:
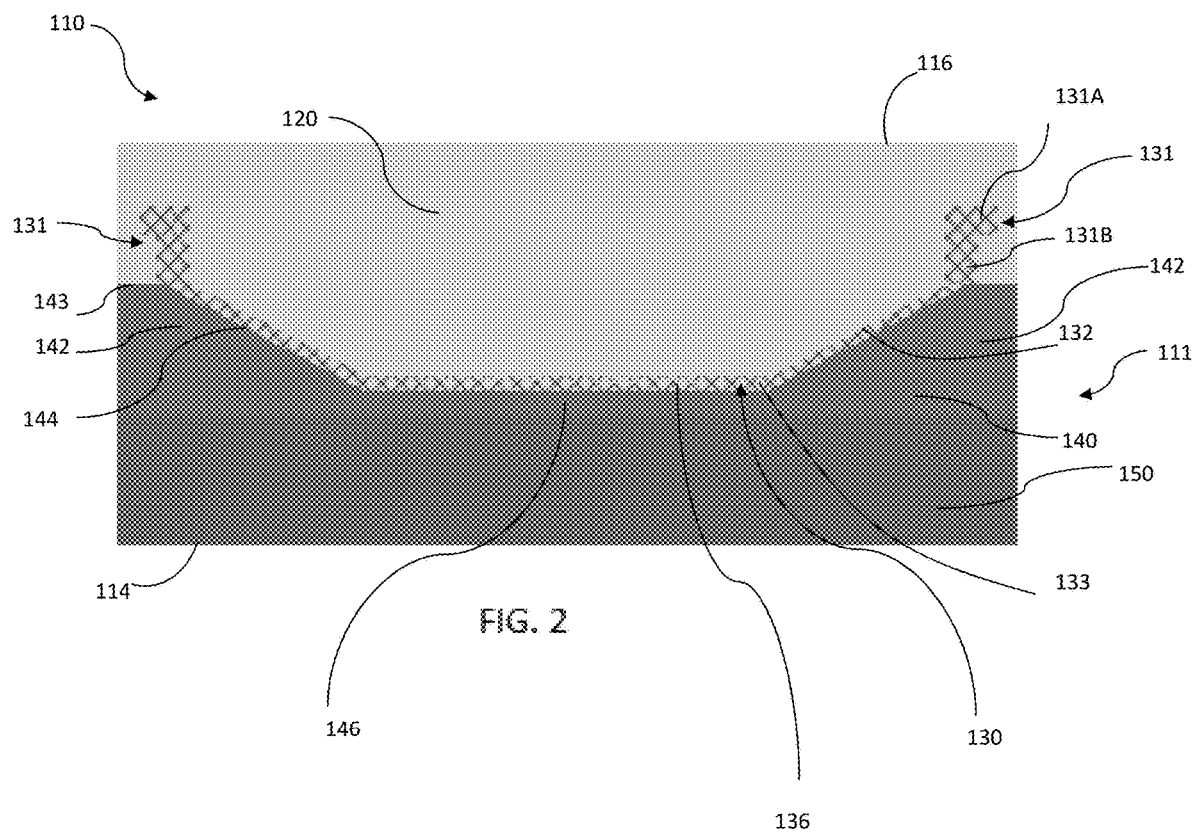
FIG. 2 is a cross-sectional elevation view of a porous structure according to an embodiment.

As shown in FIG. 2, porous structure 110, which may be any one of the medical implants as described previously herein with respect to porous structure 10, extends from a superior surface 116 to an inferior surface 114 opposite the superior surface and includes monolithic insert 111 having porous first layer 150, intermediate layer 140, and porous interlock layer 130, which may be formed serially or simultaneously using an additive manufacturing process, such as those described previously herein with respect to porous structure 10. Porous structure 110 further includes non-metallic bearing structure 120 attached to interlock layer 130, which may be integrated with the interlock layer in the same manner as described above in reference to porous structure 10.

First layer 150 may be a bone ingrowth layer having a porosity within a range that promotes bone ingrowth.

Intermediate layer 140 may be substantially the same as intermediate layer 40 with the exception that intermediate layer 140 includes central region 146 and side regions 142 disposed on lateral sides of the central region that define a chamfered interior surface of the intermediate layer. Side region 142 includes outer top surface 143, which may be flat or substantially flat, and tapered surface 144, which may be flat or substantially flat. Central region 146 is flat or substantially flat. Each side region 142 has a thickness that varies at certain points within the side region. For example, the thickness of side region 142 at a portion along outer top surface 143 is greater than a thickness of the side region at a portion along tapered surface 144. Central region 146 has a thickness that is less than the thickness of side regions 142. In other examples, tapered surface 144 may be oriented at a variety of angles with respect to a horizontal axis of porous structure 110, which in the example shown is parallel to outer top surface 143.

As further shown, porous interlock layer 130 includes central section 136, which lies along the entirety of the length of central region 146 of intermediate layer 140, and side sections 132, which lie along the entirety of the lengths of respective side regions 142 of intermediate layer 140 on a side of the intermediate layer opposite the first layer. Side sections 132 and central section 136 together form base 133 of interlock layer 130. As shown in the illustrated embodiment, base 133 may have a substantially constant thickness, although in other arrangements, the thickness of the base may vary. Interlock layer 130 further includes projection 131 projecting from each side section 132. Projection 131 includes rim 131A extending outwardly from wall 131B. As illustrated, the thickness of projection 131 may be greater than the thickness of base 133. In this manner, projection 131 reinforces the outer portion of interlock layer 130 to allow for thinner base 133 in the inner portion of the interlock layer. As in the example shown, projection 131 extends from a portion of outer top surface 143 and a portion of tapered surface 144 of side region 142. In some alternative arrangements having outer top surfaces and tapered surfaces, the projection may extend from the side region at only one of the outer top surface 143 or tapered surface 144. In still other arrangements, the intermediate layer may not include a flat surface such that the projection may extend from only a tapered surface.

Intermediate layer 140 is solid or substantially solid and thus provides a barrier between porous first layer 150 and porous interlock layer 130 such that when the polymeric material is molded into interlock layer 130, the polymeric material does not seep through and into the first layer. As a result, first layer 150 maintains its porosity after the molding of the polymeric material. Such porosity is advantageous when first layer 150 acts as a bone ingrowth layer for a medical implant.

Figure 3:
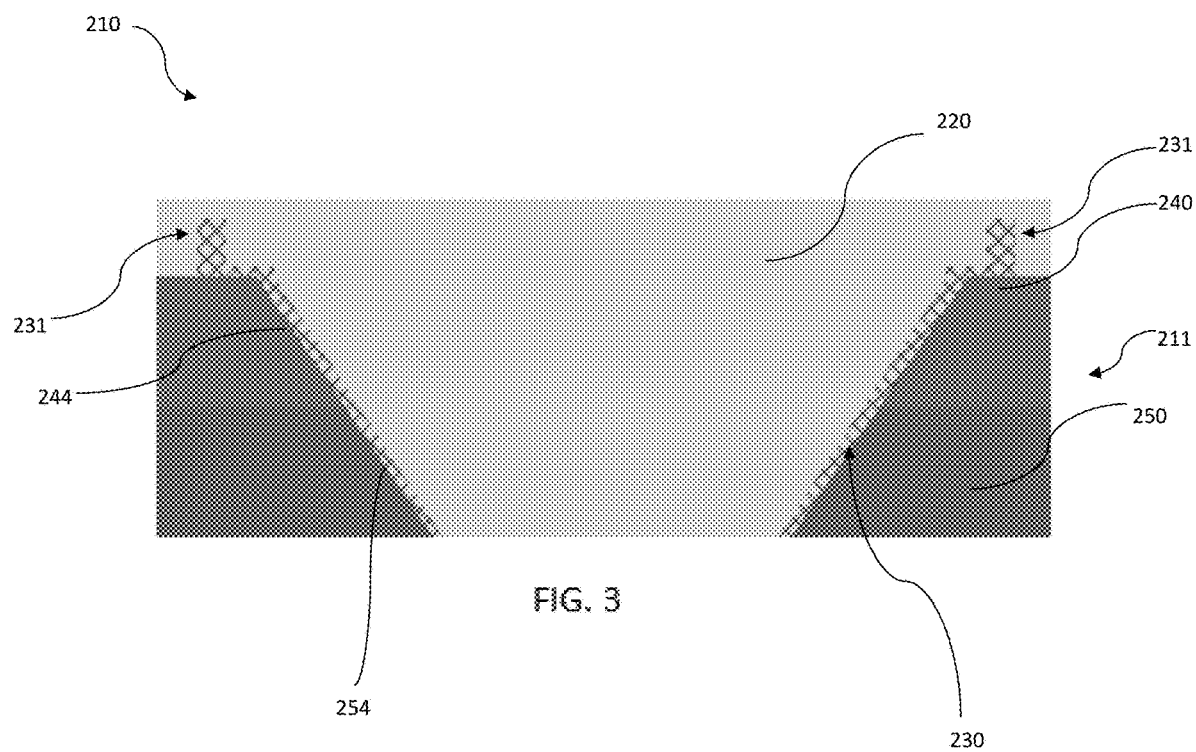
FIG. 3 is a cross-sectional elevation view of a porous structure according to another embodiment.

Referring now to FIG. 3, porous structure 210 is the same or substantially the same as porous structure 110 with the notable exception that porous structure 210 includes porous first layer 250, intermediate layer 240, interlock layer 230, and bearing structure 220. In this example, porous structure 210 is the same as porous structure 110 with the exception that, as shown, bearing structure 220 extends through the entire thickness of intermediate layer 240 and first layer 250.

Porous structure 210 includes a tapered surface similar to tapered surface 144 of intermediate layer 140 of porous structure 110. However, tapered surface 244 of intermediate layer 240 extends through the entire thickness of the intermediate layer. As a result, intermediate layer 240 does not include a central region similar to central region 146 of porous structure 110. Further, the tapered surface continues through the entire thickness of first layer 250 such that the first layer includes tapered surface 254. Thus, porous structure 210 has a maximum thickness equal to the thickness of bearing structure 220.

Projections 131, 231 of porous structures 110, 210 may increase the interlock strength of the interlock layers and may allow for mechanical interlocking of the polymeric material onto the solid material. In this manner, the thickness along a majority of the length of interlock layer 130 of porous structures 110, 210 may be less than interlock layer 130 of porous structure 10. Further, projections 131, 231 may provide structural rigidity and support to the porous structures 110, 210. Projections 131, 231 provide additional strength to the bearing structure at a point where the bearing structure is thinner. As can be seen by FIGS. 2 and 3, bearing structures 120, 220 have a decreased thickness in the area superior to side regions 142 and projections 131, 231. In this manner, projections 131, 231 provide additional support to the portion of the bearing structure 120, 220 having less thickness.

Advantageously, as in the examples of FIGS. 2 and 3, bearing structures 120, 220 of porous structures 110, 210 cover all or substantially all of corresponding interlock layers 130, 230. In such arrangements for medical implants, this configuration minimizes tissue irritation. These benefits can be achieved while the overall thickness of porous structures 110, 210 is reduced, which enables bone and soft tissue conservation. Additionally, reducing the thickness and overall amount of metal used in porous structures 110, 210 may save manufacturing costs.

As shown in FIGS. 2 and 3, projections 131, 231 are positioned within bearing structures 120, 220, respectively. In this manner, projections 131, 231 resist movement of bearing structures 120, 220 away from their respective intermediate layers, 140, 240. This minimizes the exposure of the projections to soft tissue, which may reduce the potential for corrosion of the projections. Additionally, the embedding of projections 131, 231 may reduce irritation and abrasion of the soft tissue and may minimize soft tissue ingrowth. However, in other examples, projections 131, 231 may be external to bearing structures 120, 220.

The preferred pore size of porous structures 110, 210 is between about 600 and 800 µm, which may be generated by a minimum unit cell size of between about 600 and 800 µm.

Further, in another arrangement, a feature similar to projections 131, 231 may be employed within first layers 150, 250 to enhance mechanical rigidity of the porous structure. In this arrangement, the projection may extend from any location of the first layer and may act as a porous structure for insertion into a mating structure, such as bone, providing further rigidity of the structure and a stronger mechanical connection with the mating structure. Such interfaces may allow a decreased thickness of the porous first layer, which advantageously decreases the overall profile of the porous structure. The projection on the first layer may be used as an alternative to or in addition to the projection of the interlock layer.

In another arrangement, a porous structure similar to porous structure 210 may include intermediate layer 240 continuing to extend along first layer 250 between the first layer and interlock layer 230, such that the intermediate layer is a barrier to prevent the polymeric material from seeping into the first layer.

Although porous structures 110, 210 include metal inserts 111, 211 which are monolithic, it is contemplated that the first layer, the intermediate layer, and the interlock layer are modular. In such an arrangement, the layers may be fixed to each other using bone cement or another biocompatible adhesive. Alternatively, or in addition to an adhesive, the layers may be secured using fasteners, including screws or rivets.

In alternative arrangements of the porous structures described previously herein, including porous structures 110, 210, the intermediate layer may include a solid or substantially solid barrier section along an interface between the intermediate layer and the first layer 150, a solid or substantially solid barrier section along an interface between the intermediate layer and the interlock layer, and a porous bridging section between both of the barrier sections or otherwise throughout the rest of the intermediate layer. In this manner, less material is used for the intermediate layer while at the same time still providing a barrier which may used, for example, to prevent polymeric material from seeping into the first layer. An example of such an intermediate layer is disclosed in U.S. Pat. No 8,728,387.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the claims below.

The invention claimed is:

1. An orthopedic implant comprising:
 a porous insert having a first insert portion having a first insert thickness and a second insert portion having a second insert thickness, the porous insert having a porous first layer, an intermediate layer attached to the first layer, and a porous second layer attached to the intermediate layer on a side of the intermediate layer opposite the first layer; and
 a non-metallic structure having a first non-metallic portion having a first non-metallic thickness and a second non-metallic portion having a second non-metallic thickness, the first non-metallic portion being attached to the first insert portion and the second non-metallic portion being attached to the second insert portion,
 wherein either one or both of (i) the second insert thickness is different from the first insert thickness and (ii) the second non-metallic thickness is different from the first non-metallic thickness,
 wherein the second layer includes a base having a base thickness and a porous projection extending from the base into the non-metallic structure and having a projection thickness greater than the base thickness, and wherein the first insert thickness, the second insert thickness, the first non-metallic thickness, the second non-metallic thickness, the base thickness, and the projection thickness are all defined in a same direction, wherein the base and the porous projection each include pores into which the non-metallic structure enters such that the base and the porous projection each interlock with the non-metallic structure,
 wherein the intermediate layer has a greater density than the first layer and the second layer and thereby prevents interdigitation of the non-metallic portion from the second layer to the first layer via the intermediate layer, and
 wherein a section of the second layer adjoins the first layer and the non-metallic structure.

2. The orthopedic implant of claim 1, wherein the porous projection of the porous insert has a perimeter surrounded by the non-metallic structure.

3. The orthopedic implant of claim 1, wherein the first layer is a bone ingrowth layer having a porosity sufficient to promote bone ingrowth.

4. The orthopedic implant of claim 1, wherein the orthopedic implant includes a superior surface and an inferior surface opposite the superior surface, wherein the first, the intermediate, and the second layers and the non-metallic structure each have a maximum thickness defined in superior-inferior directions along an axis passing through the superior and the inferior surfaces, the maximum thickness of the non-metallic structure being greater than the thickness of each of the other layers.

5. The orthopedic implant of claim 1, wherein the non-metallic structure is made of a polyethylene.

6. The orthopedic implant of claim 1, wherein the orthopedic implant has a superior surface and an inferior surface opposite the superior surface, a section of the non-metallic structure extending from the superior surface to the inferior surface of the orthopedic implant.

7. The orthopedic implant of claim 1, wherein the first non-metallic thickness is less than the second non-metallic thickness, and wherein the porous projection extends into the first non-metallic portion of the non-metallic structure.

8. The orthopedic implant of claim 1, wherein the insert includes a metallic tapered surface, and wherein the non-metallic structure includes a non-metallic tapered surface extending along the metallic tapered surface between the first non-metallic portion and the second non-metallic portion.

9. The orthopedic implant of claim 1, wherein the first insert portion and the second insert portion define an insert width, and wherein the non-metallic structure extends along the entirety of the insert width.

10. The orthopedic implant of claim 1, wherein the non-metallic structure is a bearing having a bearing surface.

11. The orthopedic implant of claim 1, wherein the orthopedic implant is a tibial component, a glenoid component, a patellar component, a wrist implant, a foot implant, an ankle implant, a spinal implant, or an acetabular cup.

12. The orthopedic implant of claim 1, wherein the first insert thickness and the second insert thickness are the same.

13. The orthopedic implant of claim 1, wherein the first non-metallic thickness and the second non-metallic thickness are the same.

14. The orthopedic implant of claim 1, wherein the porous insert is metallic.

15. The orthopedic implant of claim 1, wherein the intermediate layer is positioned between the first and second layers in a direction of the first insert thickness.

16. The orthopedic implant of claim 1, wherein the porous projection is defined by a plurality of struts forming cells of regular shape and extends into the non-metallic structure.

17. The orthopedic implant of claim 1, wherein the pores of the base and the porous projection are porous geometries defined by unit cells.

18. An orthopedic implant having a superior surface and an inferior surface opposite the superior surface comprising:
- a polymeric structure;
- a metallic support structure, the support structure including a base having a base thickness and a porous projection having a projection thickness greater than the base thickness, the porous projection extending from the base and into the polymeric structure, wherein the base and the porous projection each include pores into which the polymeric structure enters such that the base and the porous projection each interlock with the polymeric structure;
- an intermediate layer; and
- a porous bone ingrowth layer, the intermediate layer being located between and inseparable from the bone ingrowth layer and the support structure,
- wherein at least a portion of the polymeric structure extends through the support structure and from the superior surface to the inferior surface,
- wherein the intermediate layer has a lesser porosity than the bone ingrowth layer and the support structure and thereby prevents interdigitation of the polymeric structure across the intermediate layer into the bone ingrowth layer, and
- wherein a section of the support structure adjoins the bone ingrowth layer and the polymeric structure.

19. The orthopedic implant of claim 18, wherein the bone ingrowth layer has a porosity sufficient to promote bone ingrowth that is different than a porosity of the support structure.

20. The orthopedic implant of claim 18, wherein the orthopedic implant is a tibial implant component or a glenoid implant component.

21. The orthopedic implant of claim 18, wherein the porous projection is defined by a plurality of struts forming cells of regular shape.

22. The orthopedic implant of claim 18, wherein:
- the porous projection defines a rim that is spaced from the intermediate layer; and
- the polymeric structure extends at least between the rim and the intermediate layer.

* * * * *